USOO5981709A

United States Patent [19]
Greenwald et al.

[11] Patent Number: 5,981,709
[45] Date of Patent: Nov. 9, 1999

[54] α-INTERFERON-POLYMER-CONJUGATES HAVING ENHANCED BIOLOGICAL ACTIVITY AND METHODS OF PREPARING THE SAME

[75] Inventors: Richard B. Greenwald, Somerset, N.J.; Carl W. Gilbert, Powder Springs, Ga.

[73] Assignee: Enzon, Inc., Piscataway, N.J.

[21] Appl. No.: 08/994,623

[22] Filed: Dec. 19, 1997

[51] Int. Cl.$^6$ .......................... C07K 1/113; C07K 14/56
[52] U.S. Cl. .......................... 530/351; 530/409; 530/410
[58] Field of Search .................................. 424/85.4, 85.7; 530/351, 409, 410, 411

[56] References Cited

U.S. PATENT DOCUMENTS

| 4,179,337 | 12/1979 | Davis et al. | 435/181 |
| 4,609,546 | 9/1986 | Hiratani | 514/2 |
| 4,766,106 | 8/1988 | Katre et al. | 514/12 |
| 4,810,638 | 3/1989 | Albarella et al. | 436/547 |
| 4,894,226 | 1/1990 | Aldwin et al. | 424/85.2 |
| 4,897,471 | 1/1990 | Stabinsky | 424/85.7 |
| 4,917,888 | 4/1990 | Katre et al. | 424/85.91 |
| 5,004,605 | 4/1991 | Hershenson et al. | 530/351 |
| 5,109,120 | 4/1992 | Ueno et al. | 530/351 |
| 5,122,614 | 6/1992 | Zalipsky | 548/520 |
| 5,281,698 | 1/1994 | Nitecki | 530/351 |
| 5,382,657 | 1/1995 | Karasiewicz et al. | 530/351 |
| 5,468,478 | 11/1995 | Saifer et al. | 424/78.27 |
| 5,539,063 | 7/1996 | Hakimi et al. | 525/403 |
| 5,559,213 | 9/1996 | Hakimi et al. | 530/351 |
| 5,646,242 | 7/1997 | Baker et al. | 530/303 |
| 5,650,234 | 7/1997 | Dolence et al. | 428/447 |
| 5,676,942 | 10/1997 | Testa et al. | 424/85.7 |
| 5,711,944 | 1/1998 | Gilbert et al. | 424/85.7 |
| 5,747,646 | 5/1998 | Hakimi et al. | 530/351 |

FOREIGN PATENT DOCUMENTS

| 0 236 987 | 9/1987 | European Pat. Off. . | |
| 0 510 356 | 10/1992 | European Pat. Off. . | |
| 0 809 996 A2 | 12/1997 | European Pat. Off. | A61K 47/48 |
| 0 593 868 B1 | 4/1998 | European Pat. Off. | C07K 14/56 |
| WO96/11953 | 4/1996 | WIPO . | |

OTHER PUBLICATIONS

Goeddel, D.V. et al., *The Structure of Eight Distinct Cloned Human Leukocyte Interferon cDNAs* Nature, vol. 290; pp. 20–26; Mar. 5, 1981.

Zalipsky, S. et al., *Attachment of Drugs to Polyethylene Glycols* Eur. Polym. J., vol. 19, No. 12; pp. 1177–1183; 1983.

Zalipsky S. et al., Evaluation of a New Reagent for Covalent Attachment of Polyethylene Glycol to Proteins Biotechnology and Applied Biochemistry, vol. 15; pp. 100–114; 1992.

Kontsek, P., Human Type I Interferons: Structure and Function, Acta Virologica, vol. 38; pp. 345–360; 1994.

Kinstler, O.B. et al., Characterization and Stability of N–terminally PEGylated rhG–CSF, Pharmaceutical Res., vol. 13, No. 7; pp. 996–1002; 1996.

Monkarsh, S.P. et al., Positional Isomers of Monopegylated Interferon alpha–2a: Isolation, Characterization, and Biological Activity , Analytical Biochemistry, vol. 247; pp. 434–440; 1997.

(List continued on next page.)

*Primary Examiner*—Jeffrey E. Russel
*Attorney, Agent, or Firm*—Roberts & Mercanti, LLP

[57] ABSTRACT

A process for preparing α-interferon-polymer conjugates having high levels of retained interferon activity and relatively long circulating lives in vivo is disclosed. The process includes forming substantially non-antigenic α-interferon-polymer conjugates, combining the α-interferon-polymer conjugates with a sufficient amount of an acid to reduce the pH of the conjugates to a level which is sufficient to cleave the polymer linkages in an active site area of the interferon and thereafter adjusting the α-interferon-polymer conjugates to a physiologically-acceptable pH. Methods of treating interferon-susceptible conditions with the compositions of the present invention are also disclosed.

23 Claims, 2 Drawing Sheets

OTHER PUBLICATIONS

Viscomi, G.C., Structure–activity of Type I Interferons, Biotherapy, vol. 10; pp. 59–86; 1997.

Gotoh, Y., et al. Chemical Modification of Silk Fibroin with Cyanuric Chloride–Activated Poly(ethylene glycol): Analysis of Reaction by H–NMR Spectroscop and . . . Bioconjugate Chem, vol. 4; pp. 554–559; 1993.

Lundblad, R.L., et al. *Chemical Reagents for Protein Modification*, CRC Press, Inc., vol. 1; pp. 105–125; 1988.

Shearwater Polymers, Inc. *Catalog*, p. 45; Jan. 1996.

α-INTERFERON-POLYMER-CONJUGATES HAVING ENHANCED BIOLOGICAL ACTIVITY AND METHODS OF PREPARING THE SAME

FIELD OF THE INVENTION

The present invention is directed to long-acting interferon-containing preparations. In particular, the invention is directed to interferon conjugates having higher levels of retained biological activity, relative to the activity of previously known interferon conjugates, as well as to methods of making and using the same.

BACKGROUND OF THE INVENTION

Conjugating biologically-active proteins to polymers has been suggested to improve one or more of the properties of such proteins. Improved properties provided by conjugation of a bioactive material to a polymer include increased circulating life, increased water solubility and/or reduced antigenicity, relative to the same bioactive material in non-conjugated form. For example, some of the initial concepts of coupling peptides or polypeptides, including proteins, to polyethylene glycol (PEG) and similar water-soluble polymers, are disclosed by Davis et al., in U.S. Pat. No. 4,179,337, the disclosure of which is incorporated herein by reference. Such conjugates are usually formed by reacting a biologically active material, such as a protein, with a several-fold molar excess of an activated polymer, i.e., a polymer having a terminal linking group, without regard to where the polymer will attach to the protein.

Biologically active proteins that were among the first to be so conjugated include, e.g., insulin and hemoglobin. These proteins contain several free nucleophilic amino attachment sites, such as alpha amino groups (preferably N-terminal), epsilon amino groups and histidine residues, allowing several polymers to be attached, without significant loss of biologic activity.

In some instances, however, the conjugation reaction encounters complications. For example, conducting a conjugation reaction using excessive amounts of activated polymers can result in biologically inactive conjugates. Such inactivation can be caused by any of a number of undesirable reactions, including, for example, the formation of a linker bond to the protein that results in steric or conformational hindrance of a protein motif required for biological activity. This problem can be difficult to avoid since the polymer and protein are typically joined in solution-based reactions and there is little that can be done to preselect the points of polymer attachment.

It has been suggested that nonspecific polymer binding may be minimized by pre-blocking active sites with reversible (removable) protective materials, such as pyridoxal phosphate, but the results have been inconsistent.

Interferons (hereinafter may be referred to as "IFNs") are a group of proteins which could benefit from improved polymer conjugation techniques. One IFN species of great therapeutic potential that would especially benefit from such polymer-conjugation is alpha-interferon (hereinafter may be referred to as "α-IFN"). In the past, several polymer-interferon conjugates have been suggested. None of the prior art teachings, however, is believed to have disclosed that it was possible to selectively cleave any linkages that reduce the activity of the conjugated interferon.

U.S. Pat. Nos. 4,766,106 and 4,917,888, describe, inter alia, β-interferon-PEG conjugates. The conjugates described in the aforementioned patents use either an amide or ester linkage to join the methoxypolyethylene glycol to the interferon. Wide molar ratios of the polymer and interferon are disclosed, ranging from 0.1 to 1,000:1.

U.S. Pat. No. 4,894,226, discloses β-interferon conjugated via an amide linkage to polyproline using a flexible spacer arm. Similarly, U.S. Pat. No. 5,281,698, incorporated herein by reference in its entirety, describes, inter alia, reacting interferons with a urethane-linkage forming activated polyethylene glycol using a most preferred ratio of the polymer to the protein of 5:1. Also, U.S. Pat. No. 5,382,657, discloses forming amide or urethane-linked interferon conjugates using a polymer-protein ratio of about 3:1. Although relatively low molar excesses of the activated polymer were disclosed in these patents, there is no teaching or suggestion of controlling the location of covalent attachments between the polymer and protein or, more importantly, how to avoid forming conjugates containing polymers attached in the area of the active site. Thus, there was no mention of subjecting the conjugates to further treatment in order to enhance or regain the bioactivity lost by the conjugation reaction.

European Patent Application bearing publication No. 0 236 987 describes reacting alpha and gamma interferons with high molar excesses of alkyl-imido ester-activated polyethylene glycols. European Patent Application bearing publication No. 0 510 356 describes conjugating alpha interferon with pyridinyl carbonyl and thiocarbonyl activated PEG. In both cases, however, the resultant conjugates included species containing a wide variety of pegylated species, including a substantial amount containing more than one polymer strand per interferon molecule.

In other previous attempts to avoid loss of bioactivity following polymer conjugation, a granulocyte colony stimulating factor ("G-CSF")-polymer conjugate has been prepared by reacting G-CSF with a methoxy PEG carboxymethyl-N-hydroxy succinimidyl ester. The resulting conjugate is then treated with two molar hydroxylamine (pH 7.3) to remove "unstable" linkers, followed by a pH reduction to 3.5. Kinstler et al., 1996, *Pharmaceutical Res.* 13(7): 996–1002. The authors, however, provided no description or suggestion of attaining improved G-CSF nor have they provided any guidance regarding treatment of any other conjugates.

WO96/11953 reports that conjugates were prepared by reacting a protein, exemplified by consensus IFN, with a polymer, at an acid pH (pH 4). WO96/11953 states that this reaction selectively prevents linkage to lysine epsilon amino groups, while favoring linkage with the N-terminal alpha amino group. WO96/11953 also describes a two-step pH treatment process wherein G-CSF is reacted with a PEG at pH 8.0, followed by reduction of pH to pH 4.0, simply as a prelude to loading the product onto a separation column. No conjugates of interferon were reported to be prepared by this second method. In addition, it should be noted that WO96/11953 describes the use of an reductive alkylation reaction as preferred for the selective attachment of polymer, e.g., PEG, to the N-terminal and does not teach or suggest the advantages of an acylation reaction to attach polymers to IFN residues other than the N-terminal.

Therefore, it is believed that neither of the aforementioned Kinstler et al. references teaches or suggests preferentially removing a bioactivity-inhibiting linker bond from an active site of interferon.

In spite of the above-mentioned work in the area of interferon-polymer conjugates, improvements have been sought. In particular, it would be beneficial to provide interferon conjugates having substantially predictable and even uniform levels of bioactivity. It would also be beneficial to prepare IFN conjugates which are substantially free of polymers attached to the active site region of the interferon.

If an effective method of achieving polymer conjugation, while avoiding interference with alpha interferon bioactive sites were available, many useful α-IFN polymer conjugates could be prepared. Thus, a solution to the above-described problems would make optimally bioactive conjugates of alpha-interferon available to the art.

SUMMARY OF THE INVENTION

In order to meet these and other needs in the art, the present invention provides new conjugates of suitable polymers with interferon proteins having desirable biological activity, as well as methods of making and using the same. The methods of the invention also provide conjugates which demonstrate higher proportions of the biological activity of the native interferon proteins, relative to that produced by previously known methods.

Preferably, such interferon proteins are relatively acid stable and exhibit or have potential for at least one useful biological activity. Desirable acid stable interferon proteins preferably include α-IFN proteins.

Thus, in one aspect of the invention, methods are provided for treating polymer conjugates of acid stable α-IFN in order to selectively cleave away polymer strands on the IFN, preferably those that may reduce the bioactivity of the conjugated interferon. The process includes the steps of:

a) forming a conjugate of an acid stable α-IFN with an activated, substantially non-antigenic polymer, in solution;

b) acidifying the conjugate-containing solution of (a) to a pH level effective to selectively cleave any polymer linkages that reduce bioactivity of the conjugated interferon; and thereafter c) adjusting the acidified solution of (b) to a physiologically-acceptable pH.

The reaction of step (c) is conducted for a time period and at a pH effective to produce a product that is substantially free of conjugates having significant inhibition of native IFN bioactivity. In addition, the product of step (c) is optionally isolated from solution by any suitable art-known methods, as required. The pH lowering, e.g., acidification, is conducted with a suitable acid at a concentration and for a time such that native IFN bioactivity is substantially retained by the resulting conjugates.

The α-IFN conjugates are preferably formed by reacting a non-antigenic, carbamate-activated polymer, with α-IFN, in a molar ratio of from about 1:8 to about 8:1 (moles of polymer, per mole of IFN). More preferred molar ratios include those ranging from about 1:4 to about 4:1 moles of polymer per mole of IFN. The substantially non-antigenic polymer is preferably a polyalkylene oxide (PAO) such as a polyethylene glycol (PEG) having a molecular weight of from about 600 to about 60,000.

In accordance with another embodiment of the present invention, there are provided α-IFN-polymer conjugates which can be included as part of pharmaceutically-acceptable solutions. Conjugates that can be prepared by the above-described process include α-IFNs attached to an activated, substantially non-antigenic, polymer. Activation is preferably achieved by reacting the polymer with a carbamate-forming moiety. Without being bound by theory, Applicants believe that the carbamate linkage extends between an amino group of the IFN and a terminus of the substantially non-antigenic polymer.

In preferred embodiments, substantially all of the α-IFN-polymer conjugates of the present invention contain a single polymer strand covalently attached to the IFN molecule, e.g., are monosubstituted. While not wishing to be bound by any theory, it is believed that the aforementioned single polymer is attached so as to avoid inhibiting the bioactivity of the conjugated interferon.

Given that there are multiple possible attachment points for a polymer to acylate an interferon and given the range of acceptable molar ratios, it will be understood that, in certain embodiments, the conjugate product includes one or more polymeric strands.

In further optional embodiments, where the IFN is substituted by more than one polymer, the substitutions may range from 2 to about 8 polymers per IFN molecule.

Thus, pharmaceutical preparations can be prepared with conjugates designed to include a substantially uniform number of polymer strands per interferon molecule, while retaining maximized levels of native interferon bioactivity, relative to previously known interferon conjugates. Such previously known interferon-polymer conjugates include those prepared with large molar excesses of activated polymers and/or included polymers, conjugated to the active site of the interferon.

The invention also includes methods of treating α-interferon-susceptible conditions in mammals. In this aspect, the treatment methods include administering an effective amount of the α-interferon conjugates to mammals requiring such therapy.

As a result of the present invention, there are provided α-interferon conjugates having predictable, relatively uniform interferon activity. In one embodiment, without being bound to any theory or hypothesis, Applicants believe that this result is due to the substantially uniform presence of a single strand of polymer per conjugate, wherein, as discussed above, the single polymer strand is attached substantially away from the active site of the interferon. Another feature of the present invention is that increased circulating life is achieved with minimal losses in retained interferon activity.

For purposes of appreciating the present invention, the following terms are described:

"acid stable" shall be understood to describe a substance, including a protein such as α-interferon, that retains substantially all of its desirable properties, including its bioactive properties, when subjected to the acid pH reaction step according to the invention;

The terms "bioactive" and "biologically active" are to be considered synonymous for purposes of the present invention, unless otherwise specified. The term bioactive shall be understood to mean that the substance to which such term is applied has the property of "bioactivity", e.g., medical utility (therapeutic and/or diagnostic) in a mammal, mammalian tissues and/or mammalian cells. Thus, a bioactive interferon, or derivative and/or conjugate thereof, acts to modify or determine a state or function of a mammal, mammalian organ, tissue, cell, fluid, secretory product, and the like. Such a modification is, for example, for the purpose of providing a therapeutic medical treatment or other desired effect and/or to indicate the state or function of a mammal by means of a diagnostic test. Further, it will be understood that useful functions of a bioactive substance, such as an interferon protein or conjugate, can be obtained in vivo, ex vivo, or in vitro, as appropriate;

"bis-activated polymers" shall be understood to include polymers having alpha and omega terminal moieties which serve as suitable leaving groups during conjugation (linking) reactions with interferons;

"bis-interferon-polymer conjugates" shall be understood to describe a single strand of substantially non-antigenic polymer with two molecules of interferon covalently attached, one to the alpha terminus and one to the omega terminus of the polymer;

"carbamate" and "urethane" linkages are to be considered synonyms for purposes of the present invention;

"circulating life" shall be understood to mean the time period during which a conjugate according to the invention, or an α-interferon released from a conjugate according to the invention, remains, in vivo, at a pharmaceutically effective concentration in the circulating blood and/or plasma of a mammal, to which the conjugate has been administered.

"interferon susceptible condition" shall be understood to include all disease states, such as viral infections, immune disorders, cancers, or related conditions, which benefit therapeutically from exogenous interferon, especially α-interferon, administration;

"mono-interferon-polymer conjugates" shall be understood to describe a conjugate containing a single interferon molecule covalently attached to a terminus of a single strand of substantially non-antigenic polymer;

"physiologically-acceptable pH" shall be understood to describe a pH which is compatible with physiological systems.

For a better understanding of the present invention, reference is made to the following description and its scope will be pointed out in the appended claims.

DETAILED DESCRIPTION OF THE INVENTION

1. OVERVIEW

Figure 1:
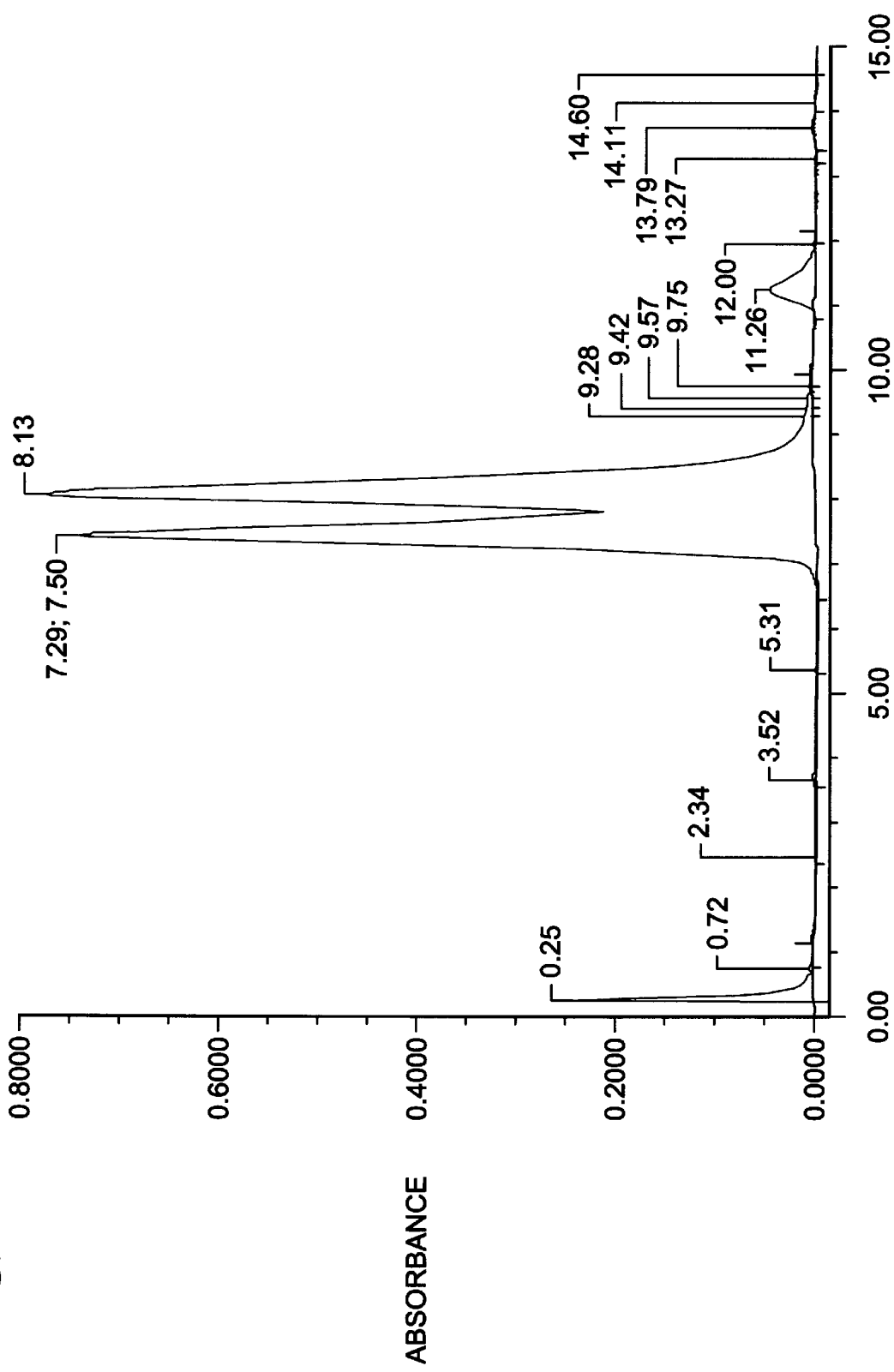
FIG. 1 is a graph of an HPLC separation of PEG-α-IFN conjugates taken prior to the selective hydrolysis process of the present invention.

Accordingly, the present invention includes a process for preparing polymer conjugates with biologically-active interferon proteins, wherein the produced conjugates retain high levels of biological activity, relative to the same interferons conjugated to the same polymer by previously used processes. In a preferred aspect, the interferon is an α-interferon protein. Thus, the process of the invention includes:

a) forming a conjugate of a polymer-linked, acid stable interferon with a substantially non-antigenic polymer, in solution;

b) acidifying the conjugate-containing solution of (a) to a pH level effective to selectively cleave any polymer linkages that reduce activity of the conjugated interferon; and thereafter c) adjusting the acidified solution of (b) to a physiologically-acceptable pH.

In a preferred embodiment, step (b) of the process, described supra, is conducted for a time period and at a pH effective to produce a conjugate product according to the invention. It is also preferred that the conjugate product is substantially free of conjugates having significant inhibition of native IFN bioactivity, e.g., inhibition caused by active site interference, steric hindrance or blockade by the linked polymer(s). The optimal time period and pH are readily determined and adjusted by the ordinary artisan, who will appreciate that such parameters are adjusted using routine methods, based on the specific polymer, activated linker, the nature of the desired conjugate, and so forth. The term, "substantially free" indicates that a significant proportion of the undesirable conjugates with activity lower than that of native IFN, are removed. Thus, the product generally includes from about 0 to about 20 percent of the described undesirable conjugates. More preferably, the product includes from about 5 to about 20 percent of the undesirable conjugates, or from about 10 to about 15 percent of the undesirable conjugates.

In a further preferred embodiment, the product of step (c) of the inventive process is preferably purified or isolated from the pH adjusted solution by any suitable art-known methods, as required. A discussion of one isolation procedure is discussed and exemplified, merely for illustrative purposes, by the text and Examples found herein below.

2. INTERFERONS

The interferons are a complex family of cytokine proteins. At present, the interferons are categorized into five different types: alpha IFN (leukocyte IFN), beta IFN (fibroblast IFN), gamma IFN (immune IFN), omega IFN and tau IFN (trophoblastic factor). For a review of the details and homology relationships of the known IFN proteins, See, e.g., Viscomi, 1997, *Biotherapy* 10:59–86, incorporated by reference herein. In addition, various recombinant and non-naturally occurring interferons have been constructed and reported. For example, human consensus IFN is a recombinantly produced alpha IFN as a consensus of specified human interferon sequences. While only alpha interferons are discussed below, the artisan will appreciate that the invention may optionally be practiced with other members of the interferon family of proteins that are usefully acid stable and that provide the required polymer attachment sites and desired biological activities.

α-Interferons

In one aspect of the invention, α-IFNs are preferred for the processes and conjugates of the present invention. In general, the α-IFN portion of the polymer conjugate can be prepared or obtained from a variety of sources including recombinant techniques, such as those using synthetic genes expressed in *E. coli*. See also Pestka, "Interferon α" in *Human Cytokines,* Blackwell Scientific Publications 1–16 (1992), the disclosure of which is incorporated herein by reference. Additional IFN's are described in "Structure-activity of Type I Interferons" *Biotherapy* 10:59–86 (1997), U.S. Pat. Nos 4,897,471, 5,541,293 and 5,661,009, the contents of each of which are incorporated herein by reference. Alternatively, the α-IFN can also be a mammalian extract such as human, ruminant or bovine α-IFN.

A number of α-IFN proteins are known. These include, for example, proteins encoded by the eight distinct cloned human leukocyte IFN cDNA reported by Goeddel et al., 1981, *Nature* 290:20–21, the disclosure of which is incorporated by reference herein. Another α-IFN is human consensus interferon. Consensus interferon is a non-naturally occurring polypeptide, that primarily includes the amino acids and peptide sequences present in all of the naturally-occurring human α-IFN subtypes. At sequence positions at which here there is no amino acid common to all subtypes, the residue that predominates among the various subtypes is selected. Additional information concerning human consensus α-IFN and methods of obtaining the same is summarized, e.g., by WO 96/11953, the disclosure of which is incorporated by reference herein.

One particularly preferred α-IFN is IFNα-2b, a recombinantly-made product of the Schering Corp., Kenilworth, N.J. Other substances, including IFN or α-IFN fractions or predecessor polypeptides or substances having an IFN effect in mammals, can also be included in the conjugates of the present invention.

As used herein, "IFN effect in mammals" means any substance which demonstrates in vivo activity corresponding to that observed with IFN's. These substances are prepared by using techniques known to those of ordinary skill in the art such as tissue culture, extraction from animal sources or by recombinant DNA methodologies. Transgenic sources of IFN and related moieties are also contemplated. Such proteins are obtained from transgenic animals, i.e., mice, pigs, cows, etc. where the IFN protein is expressed in milk, blood, or tissues. It is also understood that the recombinant techniques could also include a glycosylation site for addition of a carbohydrate moiety on the recombinantly-derived polypeptide. The method by which the IFN is prepared for the conjugates of the present invention is not limited to those described herein.

As stated above, α-IFN is preferred for the present invention not only because of its biochemical and serological properties, but also because it has documented antiviral properties and diffuses more effectively into the bloodstream than other interferons. In addition, α-interferon is acid stable so as to benefit from the methods of the invention. While not wishing to be bound by any theory, the acid catalyzed removal of undesirable polymers from α-IFN is believed to contribute to maintaining native IFN activity.

As noted above, α-IFNs according to the invention are most preferably acid stable when contacted for an effective period of time with a reaction solution having an acid pH. The pH level is sufficient to remove, hydrolyze or otherwise cleave the linkages, e.g., carbamate linkages, in an active site area of an interferon protein of interest. Suitable recombinant α-interferons which may be used in the practice of the invention include but are not limited to interferon alpha-2b such as Introns® A available from Schering Corporation, Kenilworth, N.J., interferon alpha-2a such as Roferon® A available from Hoffmann-La Roche, Nutley, N.J., and Infergen® available form Amgen, Thousand Oaks, Calif.

3. NON-ANTIGENIC POLYMER

In order to form the interferon conjugates of the present invention, substantially non-antigenic polymers such as poly(alkylene oxides) (PAO's) are converted into activated forms, as such term is known to those of ordinary skill in the art. Thus, one and preferably both of the terminal polymer hydroxyl end-groups, (i.e., the alpha and omega terminal hydroxyl groups) are converted into reactive functional groups which, in turn, allow the polymer to be covalently conjugated to a protein of interest. This process is frequently referred to as "activation" and the product is called an "activated poly(alkylene oxide)". Polymers containing both alpha and omega linking groups are referred to as bis-activated polyalkylene oxides. Other substantially non-antigenic polymers such as polypropylene glycol (PPG) and those described herein are similarly "activated" or functionalized.

The preferred activated polymers are those which form a urethane or carbamate linkage with a nucleophilic amino group, e.g., an N-terminal α-amino group, ε-amino acid group of lysine and imidazole amino group of histidine, found on IFN molecules. Preferably, the urethane linkage is formed using a terminal oxycarbonyl-oxy-N-dicarboximide group, such as a succinimidyl carbonate group. Alternative activating groups include N-succinimide, N-phthalimide, N-tetrahydrophthalimide and other such activating groups, such as benzotriazole. Thus, the substantially non-antigenic polymers include leaving groups on the alpha and/or omega terminal(s). These urethane-forming groups are described in commonly owned U.S. Pat. No. 5,122,614, the disclosure of which is incorporated by reference herein.

U.S. Pat. No. 5,122,614 also discloses the formation of N-succinimide carbonate derivatives of polyalkylene oxides including polyethylene glycols which are also capable of forming urethane linkages with lysine amino group targets. Additional groups include, p-nitrophenyl carbonate (PNP), oxycarbonylimidazole (CI) and thiazolidine thione.

Preferably, the substantially non-antigenic polymer is activated with the SC group. U.S. Pat. No. 5,122,614 also discloses the formation of mono- and bis-N-succinimidyl carbonate derivatives of polyalkylene oxides and conjugates made therewith. It will be understood, however, that regardless of the activated polymer leaving group used, the urethane or carbamate linkage reaction will proceed in a similar manner which will be apparent to the skilled artisan without undue experimentation.

Although the carbamate or urethane linkages are generally regarded in the art as being relatively hydrolysis-resistant, it has been surprisingly found that under the conditions described herein, certain carbamate bonds can be selectively cleaved. For example, while not being bound by hypothesis, it is considered to be possible that when the carbamate bond which attaches to either a lysine or histidine amino group to the polymer is located near a glutamic or aspartic acid, the free amino group of these active site region lysines or histidines are regenerated when the conjugate is exposed to a lower pH for a sufficient time, thus increasing the specific activity of the resultant conjugate, while other carbamate linkages on the protein are substantially unaffected. Although polymers can be attached to the interferon using other types of linkages, i.e., amide, urea, etc., using alternative types of activated polymers, the carbamate linkage is preferred because of its relatively unique degree of linkage strength and susceptibility to selective hydrolysis in the active site region of the interferon.

In another aspect of the invention, the group of substantially non-antigenic polymers, optionally includes the bis-activated polymers, e.g., bis-activated polyalkylene oxides (PAO's), such as bis-activated polyethylene glycols.

Suitable polymers will vary substantially by weight; however, polymers having molecular weights ranging from about 600 to about 60,000 are usually selected for the purposes of the present invention. Molecular weights of from about 1,000 to about 40,000 are preferred and 2,000 to about 20,000 are particularly preferred.

The polymeric substances employed according to the invention are also preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl pyrrolidones, polyacrylamides, polyvinyl alcohols, carbohydrate-based polymers and the like can be used. The activation of terminal groups of these polymeric substances can be effected in fashions similar to that used to convert polyalkylene oxides and thus will be apparent to those of ordinary skill. Those of ordinary skill in the art will realize that the foregoing list is merely illustrative and that all polymer materials having the qualities described herein are contemplated. For purposes of the present invention, "effectively non-antigenic" means all materials understood in the art as being nontoxic and not eliciting an appreciable immunogenic response in mammals.

4. α-INTERFERON-POLYMER CONJUGATION REACTIONS

The activated polymers are preferably used in carefully defined molar ratios in order to form the conjugates described herein. It is preferred that the carbamate-linkage forming polymer be present in molar ratio amounts which are about equal to or less than that of the interferon. Thus, the activated polymer will be present in amounts of from about 1:8 to about 8:1 (moles of polymer per mole of IFN). Other molar ratios employed according to the invention include those ranging from about 1:4 to about 4:1 moles of polymer per mole of IFN. In a further aspect, molar ratios of from about 1:2 to about 2:1 moles of polymer per mole of IFN, may be employed. The artisan will therefore appreciate that the process of the invention allows for ratios of at least about 8 moles of polymer to each mole of IFN enabling the formation of significant amounts of the desired conjugates, which can thereafter treated to maximize bioactivity and, if necessary, screened to remove higher molecular weight species.

The conjugation reaction is carried out under relatively mild conditions to avoid inactivating the interferon. Mild conditions include maintaining the pH of the reaction solution in the range of 6–8 and the reaction temperatures within the range of from about 0–30° C. and preferably about room temperature, i.e., 19–22° C. A non-limiting list of suitable buffers includes phosphate, citrate, acetate, etc. The unmodified interferon resulting from these reaction conditions can be readily recycled into future batches for additional conjugation reactions.

In an optional aspect of the invention, bis-activated forms of a polymer are used to form the interferon conjugates.

The conjugation reactions of the present invention using activated polymer initially provide a reaction mixture or pool containing mono-interferon conjugates, unreacted interferon, unreacted polymer and some high molecular weight species. The high molecular weight species include multistranded conjugates, i.e., conjugates containing a plurality of polymer strands and/or polymerized (cross-linked) PEG-IFN species, up to the maximum number of substitutions that are both desired and that can practically be achieved with a particular IFN. After the unreacted species and high molecular weight species have been removed, compositions containing primarily mono-interferon-polymer conjugates are recovered. The conjugates have at least about 20% of the biological activity associated with the native or unmodified interferon, as measured using a standard viral protection assay, such as a CPE assay with EMC virus challenging A549 human lung carcinoma cells. See, for example, Larocca, A. T., Borden, E. C., and Colby, C. B. in *Human Czokines, Handbook for Basic & Clinical Research* B. B. Aggarwal & S. U. Gutterman (eds.), Blackwell Scientific Publications, Boston, 1991, the disclosure of which is incorporated by reference herein. In preferred aspects of the invention, however, the conjugates have about 30% of the biological activity associated with unmodified interferon and most preferably, the mixture has about 40% of the biological activity associated with unmodified interferon. It is to be understood that these values for retained activity are values which are calculated prior to the acid treatment process described herein.

In an optional aspect of the invention, a surfactant is used in the conjugation processes of the present invention. Suitable surfactants include ionic-type agents such as sodium dodecyl sulfate, (SDS). Other ionic surfactants such as lithium dodecyl sulfate, quaternary ammonium compounds, taurocholic acid, caprylic acid, decane sulfonic acid, etc., can also be used. Non-ionic surfactants such as polyoxyethylene sorbitans (Tweens), polyoxyethylene ethers (Tritons) can also be used. See also Neugebauer, *A Guide to the Properties and Uses of Detergents in Biology and Biochemistry* (1992) Calbiochem Corp. The only limitations on the surfactants used in the processes of the invention are that they are used under conditions and at concentrations that do not cause substantial irreversible denaturation of the interferon and do not completely inhibit polymer conjugation. The surfactants are present in the reaction mixtures in amounts from about 0.01–0.5%; preferably from 0.05–0.5%; and most preferably from about 0.075–0.25%. Mixtures of the surfactants are also contemplated.

A representative conjugation reaction is set forth below:

An about 2-fold molar excess of a carbamate-linkage forming activated polymer is dissolved in Water For Injection (pH approximately 6.0) and then added to an interferon solution adjusted to about pH 6.5–7.2 with a phosphate buffer or other suitable buffer. The reaction is allowed to incubate at room temperature (approximately 20–25° C.) for a suitable time, such as about 2 hours, with continuous gentle mixing. It will be appreciated that if more activated polymer is used, it will be more likely that the resultant conjugates will contain more than one polymer strand.

The average number of strands included as part of the conjugate can be determined by the skilled artisan, without undue experimentation. In the same spirit, the optimal number of strands per conjugate and/or optimal average number of strands per conjugate, will be readily determined by the skilled artisan, simply by conducting routine evaluations of the potency and efficacy of the conjugate for the intended use.

Thereafter, the conjugation reaction is stopped with a several-fold molar excess of glycine. The unmodified interferon present in the reaction pool, after quenching can be recycled into future reactions using ion exchange or size exclusion chromatography or similar separation techniques. Preferably, the compositions of the present invention contain less than about 5% unmodified interferon.

5. ENHANCEMENT OF POLYMER CONJUGATE INTERFERON BIOACTIVITY

After the desired polymer-interferon conjugates have been prepared and if necessary, purified, or separated from unwanted reaction products, the conjugates are treated to remove substantially all polymers, interfering with the active site region, to increase the interferon activity of the conjugate. Therefore, in this aspect of the invention, the process includes:

Forming a conjugate of an acid stable α-IFN with an activated, substantially non-antigenic polymer, in solution, and then adjusting (e.g., acidifying) to a pH level effective to selectively cleave any linkages present at or adjacent to an α-IFN active site. Thereafter, the pH of the acidified solution is adjusted to a physiologically acceptable value.

The conjugates are typically kept in an aqueous buffered solution after conjugation and purification at about pH 6.0–7.5. The solution is then transferred, if necessary, to a suitable vessel to which the acid can be added. A non-limiting list of suitable acids includes haloacetic acids such as trifluoroacetic acid, acetic acid, hydrochloric acid, sulfuric acid, phosphoric acid etc. The amount of acid added to the conjugates is described as a pH reducing amount. This amount will depend upon several factors including the type of acid selected, acid strength or concentration, and the particular α-IFN protein, etc. The amount can further be described as that amount which is sufficient to achieve the desired pH reduction and active site region selective hydrolysis without causing significant irreversible denaturation or unfolding of the interferon.

In preferred aspects of the invention, the pH of the acid-containing solution is reduced to less than about 5, more preferably to less than about 4 and most preferably to less than about 3. Thus, the pH of the acid containing or acidified solution will range from a pH of about 1 to about 4 and more preferably from a pH of about 1 to about 3. As will be appreciated by the artisan, the optimal pH range will be readily determined by routine manipulation and without undue experimentation, by conducting the process and quantifying the quality and quantity of the yield, depending upon the particular reaction conditions and, e.g., the conjugates to be treated. Similarly, the other parameters of the conjugation reaction, especially the acidification step, are readily optimized.

The time during which the conjugates are exposed to the lower pH is generally regarded as a time which is sufficient to achieve the desired result while avoiding deleterious effects on the interferon. The exact time will vary depending upon the batch size, type of acid used and other process parameters which will be apparent to the ordinary skilled artisan. It is contemplated that time periods of from about 2 minutes to about 7 hours will generally be regarded as sufficient for achieving sufficient selective hydrolysis without significant irreversible protein denaturation. More preferably, a time period of from about 2 minutes to about 4 hours is employed, or even a time period from about 1 to about 4 hours.

As pointed out above, while Applicants are not bound by theory, it is believed that bioactivity enhancement provided by the acid treatment takes place by cleavage of a carbamate modified nucleophilic amino group. The cleaved carbamate group is possibly one that causes interference with interferon bioactivity, e.g., by blocking or interfering with an active site, or perhaps the interferon structure or conformation in some way.

After the selective hydrolysis reaction step, the acid-treated interferon substantially non-antigenic polymer conjugates are returned to a physiologically acceptable pH, i.e., from about 6.5 to about 7.5.

6. ISOLATION OF CONJUGATES

In a further optional embodiment of the invention, the various interferon-polymer species, i.e., mono or polystranded conjugates, are isolated. This step can be carried out either prior to, or preferably, after the acid treatment step. Separation is effected by placing the mixed species in a buffer solution containing from about 1–10 mg/ml of the interferon-polymer conjugates. Suitable solutions have a pH of from about 6.0 to about 9.0 and preferably from about 7.5 to about 8.5. The solutions preferably contain one or more buffer salts selected from KCl, NaCl, $K_2HPO_4$, $KH_2PO_4$, $Na_2HPO_4$, $NaH_2PO_4$, $NaHCO_3$, $NaBO_4$, and NaOH. Sodium phosphate buffers are preferred.

Depending upon the reaction buffer, the interferon polymer conjugate solution may first have to undergo buffer exchange/ultrafiltration to remove any unreacted polymer. For example, the PAO-interferon conjugate solution can be ultra-filtered across a low molecular weight cut-off (10,000 to 30,000 Dalton) membrane to remove most unwanted materials such as unreacted polymer, surfactants (if present), or the like.

The fractionation of the conjugates into a pool that includes substantially isolated desired product, e.g., mono-substituted polymer-IFN, is preferably carried out using an anion exchange chromatography medium. Such media are capable of selectively binding PAO-interferon conjugates via differences in charge which vary in a somewhat predictable fashion. For example, the surface charge of α-IFN is determined by the number of available charged amino acids on the surface of the protein. Of these charged amino acids, nucleophilic amino groups, e.g., alpha amino groups, lysine residues and/or histidine residues serve as the point of potential attachment of polyalkylene oxide conjugates. Therefore, various interferon conjugate species will have a different charges and allow selective isolation.

The use of strongly polar anion exchange resins such as quaternary amine anion exchange resins are especially preferred for the method of the present invention. Included among the commercially available quaternary anion exchange resins suitable for use with the present invention are Q-HD, QA TRISACRYLO and QMA-SPHEROSIL®, quaternary amine resins coated onto a polymer matrix, manufactured by IBF of Garenne, France, for Sepracor of Marlborough, Mass.; TMAE650M®, a tetramethylamino ethyl resin coated onto a polymer matrix, manufactured by EM-Separators of Gibbstown, N.J.; QAE550C®, and SUPERQC®, each a quaternary amine resin coated onto a polymer matrix and manufactured by TosoHaas of Montgomeryville, Pa. QMA Accell, manufactured by Millipore of Millford, Mass. and PEI resins manufactured by JT Baker of Phillipsburg, N.J., may also be used. Other suitable anion exchange resins e.g., DEAE resins can also be used.

For example, the anion exchange resin is preferably packed in a column and equilibrated by conventional means. A buffer having the same pH and osmolality as the polymer conjugated interferon solution is used. The elution buffer preferably contains one or more salts selected from KCl, NaCl, $K_2HPO_4$, $KH_2PO_4$, $Na_2HPO_4$, $NaH_2PO_4$, $NaHCO_3$, $NaBO_4$ and $(NH_4)_2CO_3$. The conjugate-containing solution is then adsorbed onto the column with the high molecular weight species and unreacted polymer not being retained. At the completion of the loading, a gradient flow of an elution buffer with increasing salt concentrations is applied to the column to elute the desired fraction of polyalkylene oxide-conjugated interferon. The eluted pooled fractions are preferably limited to uniform mono- and bis-interferon polymer conjugates after the anion exchange separation step. Any unconjugated interferon species can then be back washed from the column by conventional techniques. If desired, mono- and bis-interferon species can also be separated from each other via additional ion exchange chromatography or size exclusion chromatography.

Techniques utilizing multiple isocratic steps of increasing concentration can also be used. Multiple isocratic elution steps of increasing concentration will result in the sequential elution of mono- and then, in optional embodiments, bis-interferon-polymer conjugates.

The temperature range for elution is between about 4° C. and about 25° C. Preferably, elution is carried out at a temperature of from about 6° C. to about 22° C. For example, the elution of the PAO-α-IFN fraction is detected by UV absorbance at 280 nm. Fraction collection may be achieved through simple time elution profiles.

7. METHODS OF TREATMENT

Another aspect of the present invention provides methods of treatment for various disease conditions in mammals. The methods include administering an effective amount of interferon-polymer conjugates, which have been prepared as described herein, to a mammal in need of such treatment. The conjugates are useful for, among other things, treating interferon-susceptible diseases or conditions which would respond positively or favorably, as these terms are known in the medical arts, to interferon-based therapy. Thus, without limitation, the interferon conjugates can be used to treat conditions which would benefit from the inhibiting replication of interferon-sensitive viruses. In addition, the conjugates can be used to modify various immune responses including inhibition of antibody response to antigenic challenge, inhibition of hypersensitivity reactions, regulation of NK cell activity enhancement of cytotoxic T cell activity, modulation of prostaglandin production and enhancement of phagocytosis by macrophages.

Additional conditions in which the interferon-polymer conjugates can be used include hairy cell leukemia, venereal or genital warts (condylomata acuminata), AIDS-Related Kaposi's sarcoma, hepatitis and hepatitis-like viral conditions including hepatitis-B and chronic hepatitis non-A, non-B/C, and various solid tumors. The artisan will understand that the treatment afforded by the conjugates of the invention can be, for example, palliative, e.g., providing some control or relief from the effects of a condition, as well as fully or partially curative of any disease or condition so treated.

Further, any condition for which interferon administration is diagnostic is also contemplated to be within the scope of the invention.

The amount of the interferon-polymer conjugate administered to treat the conditions described above is based on the interferon activity of the polymeric conjugate. It is an amount that is sufficient to significantly effect a positive clinical response. The maximal dose for mammals including humans is the highest dose that does not cause clinically-important side effects. For purposes of the present invention, such clinically important side effects are those which would require cessation of therapy due to severe flu-like symptoms, central nervous system depression, severe gastrointestinal disorders, alopecia, severe pruritus or rash. Substantial white and/or red blood cell and/or liver enzyme abnormalities or anemia-like conditions may also be dose limiting.

Naturally, the dosages of the interferon-based compositions will vary somewhat depending upon the interferon moiety and polymer selected. In general, however, the conjugate is administered in amounts ranging from about 100,000 to about several million $IU/m^2$ of interferon per day, based on the mammal's condition. The range set forth above is illustrative and those skilled in the art will determine the optimal dosing of the conjugate selected based on clinical experience and the treatment indication.

The IFN-polymer conjugates and compositions containing the mono- and bis-interferon polymer conjugates of the present invention can be included in one or more suitable pharmaceutical compositions for administration to mammals. The pharmaceutical compositions may be in the form of a solution, suspension, tablet, capsule or the like, including, e.g., lyophilized product readily reconstituted, prepared according to methods well known in the art. It is also contemplated that administration of such compositions will be chiefly by the parenteral route although oral or inhalation routes may also be used depending upon the needs of the artisan.

8. EXAMPLES

The following examples serve to provide further appreciation of the invention but are not meant in any way to restrict the effective scope of the invention.

Example 1

In this example, succinimidyl carbonate-activated polyethylene glycol, molecular weight 12,000, was used to modify alpha interferon. The succinimidyl carbonate activated PEG was prepared in accordance with the method of the aforementioned U.S. Pat. No. 5,122,614. The interferon was recombinant α-IFN-2b, (rα-IFN), a product of the Schering- Plough Corporation, Madison, N.J.

Interferon alpha (0.28 μmoles 5 mg) was adjusted to pH 6.5 with 100 mM phosphate buffer. The activated PEG was dissolved in Water For Injection (pH approximately 6.0) and then added to the alpha interferon in a ratio of about one-half mole of activated polymer per mole of interferon. The reaction was incubated at room temperature (21° C.) for about 2 hours with continuous gentle mixing. After 2 hours, the reaction was stopped with a ten-fold molar excess of glycine. The reaction products were analyzed via SEC-HPLC (BioRad, Bio-Sil SEC-125 column) at a flow rate of 1.0 ml/minute using a 0.1 molar phosphate buffer, pH 7.0 with detection at 280 nm. The results of HPLC analysis are set forth in FIG. 1 which shows two peaks at 7.29 and 8.13, indicating that the conjugates were largely 1-PEG and 2-PEG species. A minor amount of higher molecular weight species was also detected

Example 2

Figure 2:
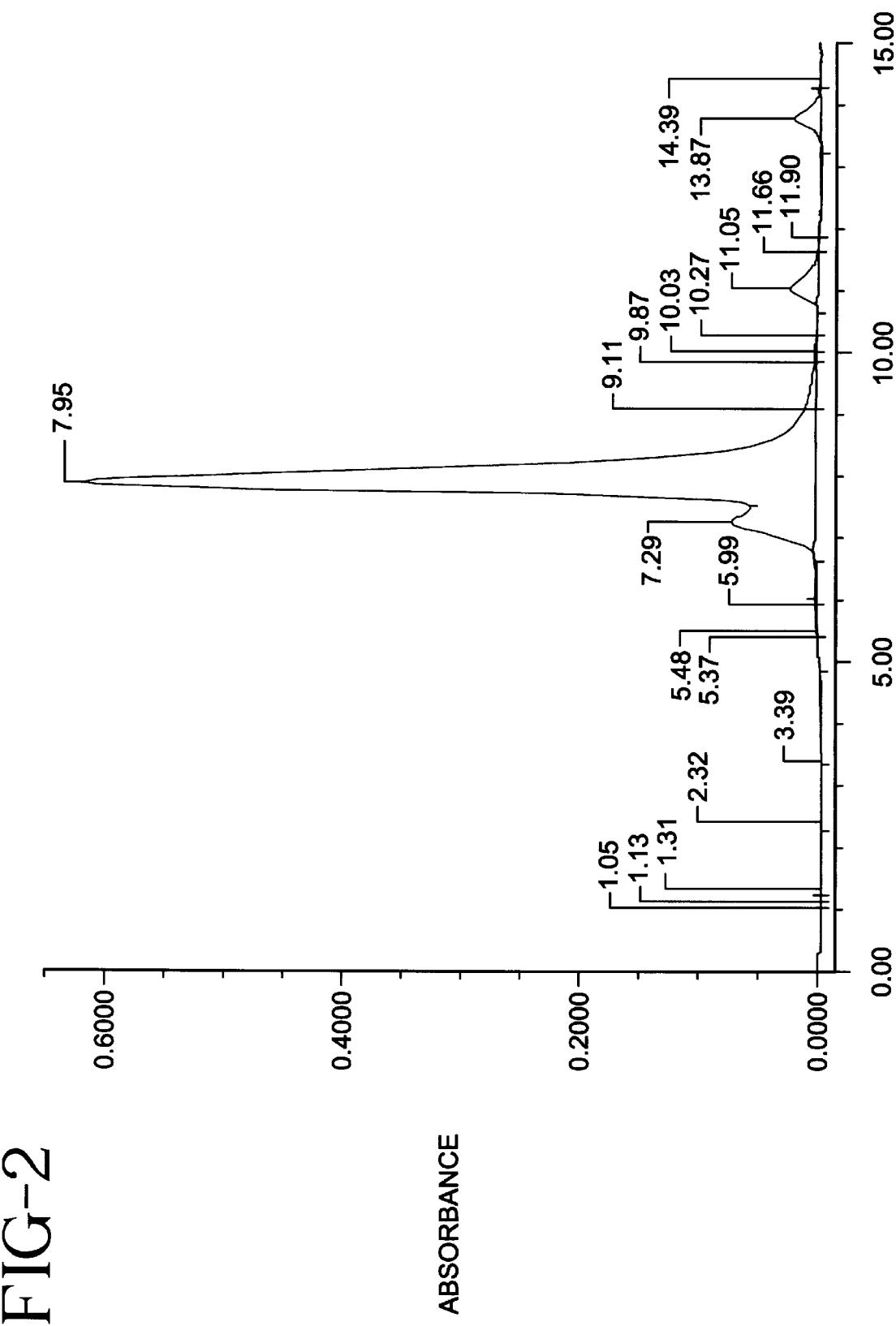
FIG. 2 is a graph of an HPLC separation of PEG-α-IFN conjugates taken after the selective hydrolysis process of the present invention.

In this example, the $PEG_{12,000}$-IFN conjugate pool containing the 1-PEG and 2-PEG conjugates resulting from Example 1 was treated with 0.1% trifluoroacetic acid to reduce the pH of the conjugates to about 1.6 for about 3 hours at 37° C. The reaction was stopped by the addition of sodium phosphate buffer (100 mM) pH 6.5, and the final pH of the solution was between pH 6.0–6.2. The acid-treated conjugates were analyzed via HPLC (100 mM sodium phosphate buffer pH 7.0). The results are set forth in FIG. 2 which illustrates a much sharper peak at 7.95 and smaller shoulder as well as some native IFN. This also indicates that the acid treated conjugates were largely the 1-$PEG_{1200}$-IFN. This fraction was collected, concentrated by a Centricon concentrator, purified by HPLC using a size exclusion column and assayed using the CPE Assay for activity. The results were compared to the values obtained by assaying the conjugates of Example 1 which did not undergo the acid treatment step. Control represents the unmodified interferon.

The comparative results are set forth in the following table:

Summary of PEG$_{12,000}$-IFN Activities

| Sample (concentration) | CPE activity | % Control (unmodified IFN) |
|---|---|---|
| ≧2 PEG$_{12000}$-IFN (2 mg/mL) | 6.53 pg/mL | 7.7% |
| 1 PEG$_{12000}$-IFN (0.1 mg/mL) | 1.74 pg/mL | 29.0% |

From the foregoing, it can be seen that the acid-treated conjugates had a significant improvement in retained activity and that this treatment step did not denature the interferon.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention. Various references have been mentioned throughout the foregoing specification, the contents of which are hereby incorporated herein in their entireties.

What is claimed is:

1. A process for preparing α-interferon-polymer conjugates, comprising:
   a) forming a conjugate of an acid stable α-interferon with an activated, substantially non-antigenic polymer, in solution;
   b) acidifying the conjugate-containing solution of (a) to a pH level of less than about 3 that is effective to selectively cleave any linkages that reduce activity of the conjugated interferon; and thereafter
   c) adjusting the acidified solution of (b) to a physiologically-acceptable pH, wherein the molar ratio of said substantially non-antigenic polymer to said α-interferon ranges from about 8:1 to about 1:8, in said solution.

2. The process of claim 1, wherein the non-antigenic polymer is activated with a carbamate-linkage forming moiety.

3. The process of claim 2, wherein said carbamate-linkage forming moiety is selected from the group consisting of oxycarbonyl-oxy-N-dicarboximide, para nitroaryl carbonates, carbonyl diimidizol, benzotriazole carbonates, and pyridyl carbonates.

4. The process of claim 3, wherein said oxycarbonyl-oxy-N-dicarboximide is a succinimidyl carbonate.

5. The process of claim 1, wherein said substantially non-antigenic polymer is activated with a succinimidyl carbonate.

6. The process of claim 1, wherein the molar ratio of said substantially non-antigenic polymer to said α-interferon ranges from about 4:1 to about 1:4.

7. The process of claim 1, wherein the molar ratio of said substantially non-antigenic polymer to said α-interferon ranges from about 2:1 to about 1:2.

8. The process of claim 1, wherein said substantially non-antigenic polymer comprises a polyalkylene oxide.

9. The process of claim 8, wherein said polyalkylene oxide comprises a polyethylene glycol.

10. The process of claim 1, wherein the solution is acidified with an acid selected from the group consisting of haloacetic, acetic, hydrochloric, sulfuric, and phosphoric acids.

11. The process of claim 10, wherein the haloacetic acid is trifluoroacetic acid.

12. The process of claim 1, wherein the pH level of step (b) is less than about 2.

13. The process of claim 12, wherein the pH level is less than about 1.6.

14. The process of claim 1, wherein the pH level of step (b) ranges from about 1 to about 3.

15. The process of claim 1, wherein said substantially non-antigenic polymer portion of said conjugates has a molecular weight of from about 600 to about 60,000.

16. The process of claim 15, wherein said substantially non-antigenic polymer portion of said conjugates has a molecular weight of from about 1,000 to about 40,000.

17. The process of claim 15, wherein the substantially non-antigenic polymer portion of said conjugates has a molecular weight of from about 2,000 to about 20,000.

18. The process of claim 1, wherein said physiologically-acceptable pH ranges from about 6.5 to about 7.5.

19. The process of claim 1, wherein said α-interferon is α-interferon 2b.

20. The process of claim 1, wherein said α-interferon is a human interferon.

21. The process of claim 20, wherein said interferon is human consensus interferon.

22. The process of claim 1, wherein said substantially non-antigenic polymer is selected from the group consisting of dextran, polyvinyl pyrrolidones, polyacrylamides, polyvinyl alcohols and carbohydrate-based polymers.

23. The process of claim 1 further comprising substantially isolating and purifying the product of step (c).

* * * * *